(12) United States Patent
Manke et al.

(10) Patent No.: US 8,882,719 B2
(45) Date of Patent: Nov. 11, 2014

(54) SYRINGE HAVING A REMOVABLE COVER FOR USE AS A PLUNGER ROD IN ROTATIONAL ENGAGEMENT

(71) Applicant: Becton Dickinson France, S.A.S., Le Pont-de-Claix (FR)

(72) Inventors: Darrin Scott Manke, North Andover, MA (US); Christopher Labak, Brookline, NH (US); Joseph Omer St. Cyr, Salem, NH (US)

(73) Assignee: Becton Dickinson France S.A.S., Le Pont-de-Claix (FR)

( * ) Notice: Subject to any disclaimer, the term of this patent is extended or adjusted under 35 U.S.C. 154(b) by 68 days.

(21) Appl. No.: 13/622,389

(22) Filed: Sep. 19, 2012

(65) Prior Publication Data

US 2013/0085447 A1    Apr. 4, 2013

Related U.S. Application Data

(60) Provisional application No. 61/541,379, filed on Sep. 30, 2011.

(51) Int. Cl.
*A61M 5/00* (2006.01)
*A61M 5/315* (2006.01)
*A61M 5/50* (2006.01)

(52) U.S. Cl.
CPC . *A61M 5/31515* (2013.01); *A61M 2005/31518* (2013.01); *A61M 5/5086* (2013.01)
USPC .......................................................... 604/187

(58) Field of Classification Search
USPC ........................... 604/187, 110–111; 206/571
See application file for complete search history.

(56) References Cited

U.S. PATENT DOCUMENTS

| 4,011,868 | A | 3/1977 | Friend | |
| 2008/0015513 | A1* | 1/2008 | Westbye et al. | 604/192 |
| 2008/0103455 | A1* | 5/2008 | Domkowski et al. | 604/232 |
| 2011/0046603 | A1 | 2/2011 | Felsovalyi et al. | |
| 2012/0214124 | A1* | 8/2012 | McLelland et al. | 433/90 |

FOREIGN PATENT DOCUMENTS

| WO | 97/29798 A1 | 8/1997 |
| WO | 2006/036122 A1 | 4/2006 |

* cited by examiner

*Primary Examiner* — Nicholas Lucchesi
*Assistant Examiner* — Melissa A Snyder
(74) *Attorney, Agent, or Firm* — The Webb Law Firm

(57) ABSTRACT

A syringe assembly includes a syringe barrel defining a chamber, a stopper disposed within the chamber, and a plunger assembly. The plunger assembly includes an elongated plunger rod, a housing, and a handle portion connecting the plunger rod and housing. The plunger assembly transitions from a first position disposed about the syringe barrel, to a second position with the plunger rod engaged with the stopper. Transition of the plunger assembly includes rotational engagement of the plunger rod and stopper.

23 Claims, 14 Drawing Sheets

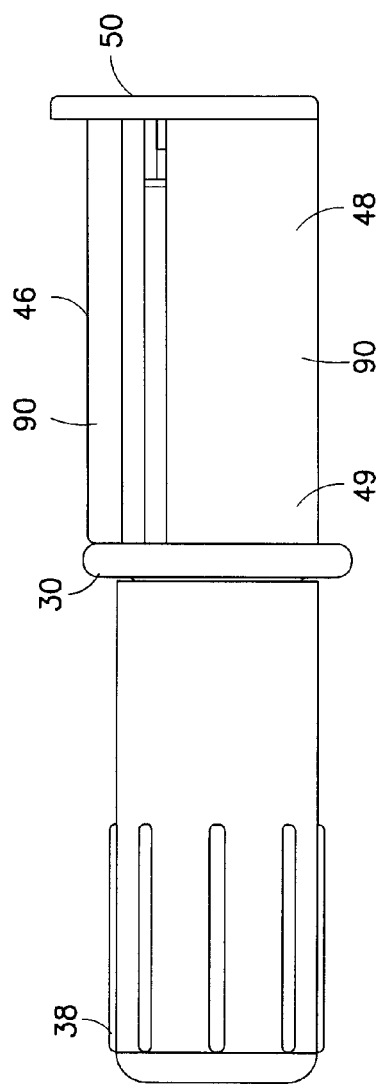
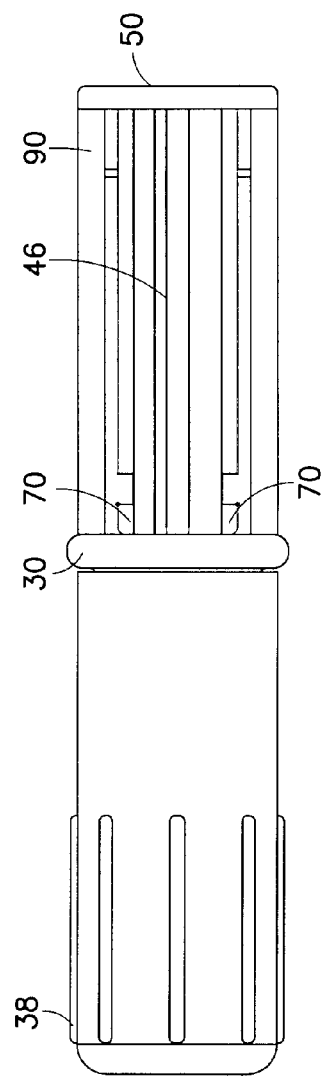

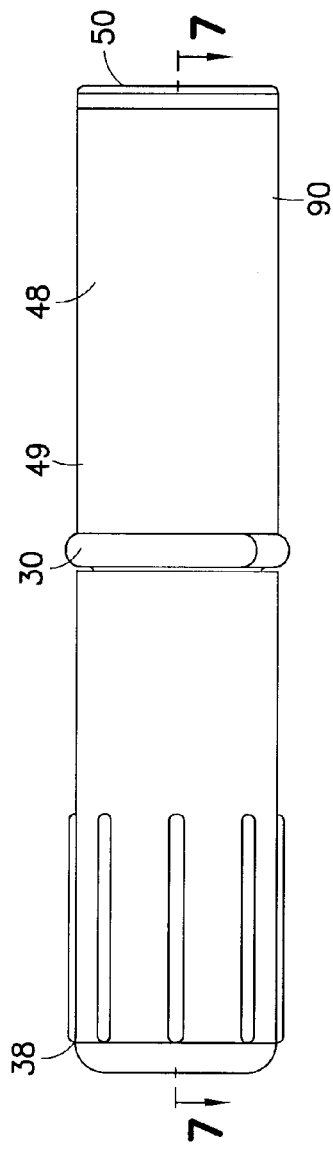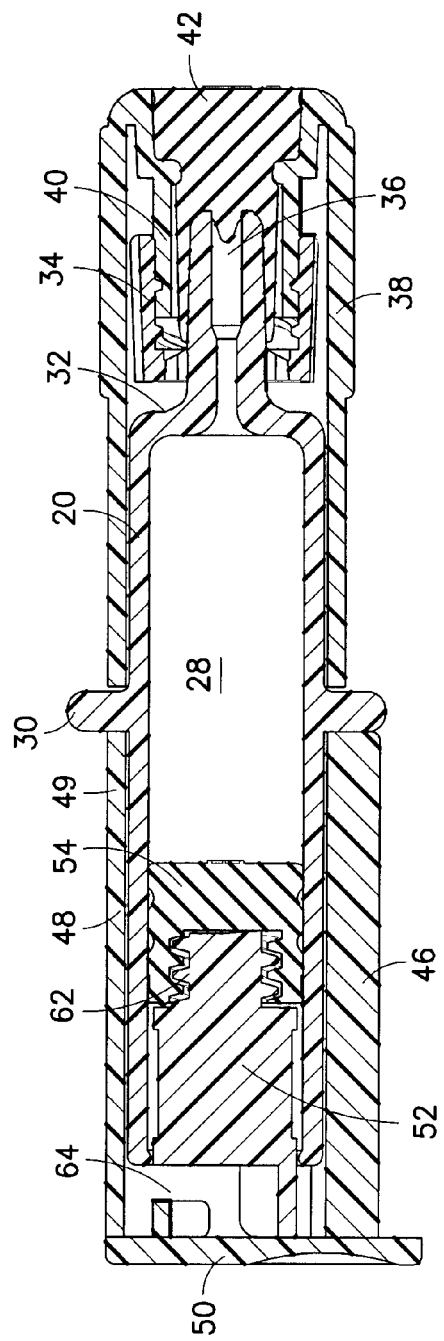
FIG.6
FIG.7

SYRINGE HAVING A REMOVABLE COVER FOR USE AS A PLUNGER ROD IN ROTATIONAL ENGAGEMENT

CROSS-REFERENCE TO RELATED APPLICATION

This application claims priority to U.S. Provisional Application Ser. No. 61/541,379 filed Sep. 30, 2011, the entire disclosure of which is hereby incorporated by reference.

BACKGROUND OF THE INVENTION

1. Field of the Invention

The present invention relates to a syringe assembly having a smaller packaging footprint allowing for reduced storage space and, more specifically, relates to a syringe assembly having a removable cover for use as a plunger rod.

2. Description of Related Art

Syringe assemblies, and in particular hypodermic syringes, are well known in the medical field for dispensing fluids, such as medication. A conventional syringe typically includes a syringe barrel with an opening at one end and a plunger mechanism disposed through the other end. The plunger mechanism typically includes a plunger rod extending through the barrel, with a plunger head or stopper at the end of the plunger rod within the barrel, and a finger flange at the other end of the plunger rod extending out of the barrel. In use, the plunger rod is retracted through the syringe barrel to aspirate or fill the syringe barrel with a fluid, such as a medication, with the plunger rod extending out from the rear end of the syringe barrel. For delivery of the medication to a patient, the opening of the syringe barrel is adapted for fluid communication with a patient, such as through a hypodermic needle fitted at the front end of the syringe barrel or through a luer-type fitting extending from the front end of the syringe barrel for attachment with a fluid line of a patient. Upon depressing of the plunger rod, the plunger rod and stopper travel through the syringe barrel, thereby forcing the contents of the syringe out through the opening at the front end for delivery to the patient. Such an operation is well known in the medical field, and medical practitioners have become well accustomed to the use of such common fluid delivery procedures through standard syringes.

Conventional syringes are well known to be used in connection with a vial of a medication, where the user draws the fluid into the syringe immediately prior to injection and delivery of the fluid to the patient. Oftentimes, hypodermic syringes may be packaged as "pre-filled" devices, wherein the syringe is pre-filled with medication prior to being packaged and delivered to the end user. In this manner, there is no need for the user to fill the device prior to injection, thereby saving time for the end user and maintaining consistent volumes for delivery.

Packaging of such pre-filled syringes, however, tends to be bulky. A pre-filled syringe is typically packaged with the opening at the front end of the barrel including a separate cap thereover and with the plunger rod retracted out of the back end of the syringe barrel, with the fluid pre-filled within the syringe barrel. Such packaging creates an elongated package that can be awkward for shipping and storage.

Pre-filled syringes and pre-filled metered dose syringes are often filled with narcotics or other drugs at a production facility, packaged, and then shipped to a medical facility. Once at the facility, these syringes are often placed in controlled storage and/or locked cabinets to reduce theft of the syringes themselves and/or theft of the contents of these syringes. The space within these controlled storage locations is often limited, thus there is a need for a syringe assembly that has a smaller packaging footprint, to reduce the storage space required for containing the syringe. A smaller packaging footprint is also beneficial for end users who may carry the syringe with them in a pocket, purse, or the like. It is also desirable to produce syringes that are uniform in terms of an outer surface shape to allow for stacking of these syringes within the storage cabinet.

Typical pre-filled hypodermic syringes have elongated plunger rods extending from beyond the proximal end of a syringe barrel to move the stopper through an injection cycle within the syringe barrel by linear actuation of the elongated plunger rod. This arrangement increases the length of the packaged syringe assembly, which increases costs associated with packaging the pre-filled syringe, and takes up additional storage space.

SUMMARY OF THE INVENTION

Accordingly, there is a general need for a hypodermic syringe that has a reduced length and reduced packaging space when the syringe barrel is filled with a liquid medication or drug prior to injection.

In the syringe assembly of the present invention, the plunger rod is adapted to transition from the pre-use position in which the plunger rod extends substantially parallel to and adjacent with the sidewall of the syringe barrel, to the expanded ready-to-use position in which the plunger rod extends substantially in line with the longitudinal axis of the syringe barrel and stopper.

It can be appreciated that the syringe assembly of the present invention can be used with any type of syringe assembly, particularly those which are placed in a controlled storage environment in which storage space is limited. These types of syringes include traditional pre-filled syringe assemblies, metered dose syringes, aspiration syringes for withdrawing fluid from a patient or medication from a container, and the like.

According to an embodiment of the present invention, a syringe assembly includes a syringe barrel having a first end, a second end, and a sidewall extending therebetween having an exterior surface and an interior surface defining a chamber therein. The syringe assembly also includes a stopper disposed within the chamber and a plunger assembly. The plunger assembly includes an elongated plunger rod, a housing, and a handle portion connecting the elongated plunger rod and the housing. The plunger assembly is adapted to transition from a first position in which the plunger assembly is disposed about the exterior surface of the syringe barrel, to a second position in which the plunger rod is engaged with the stopper. Transition of the plunger assembly from the first position to the second position includes a rotational engagement of the plunger rod with a portion of the stopper.

In one configuration, the elongated plunger rod, the housing, and the handle portion are a unitary assembly. The unitary assembly may be proximally advanced over the syringe barrel prior to the rotational engagement of the plunger rod and the stopper. In certain configurations, the stopper includes a plunger adapter and the plunger rod engages the plunger adapter in the second position. The plunger rod may be configured to advance the stopper from a first position to a second position within the barrel, wherein the first position is different from the second position.

The plunger rod may extend substantially parallel with the exterior surface of the syringe barrel in the first position, and may extend substantially in line with a longitudinal axis of the syringe barrel in the second position. The syringe assembly may include a luer connection engaged with the first end of the syringe barrel, and a cap adapted to seal the first end of the syringe barrel. A tamper evident band may be disposed over a portion of the cap and the plunger assembly.

In another configuration, the plunger rod includes a protruding member adjacent a distal end, and the stopper includes a corresponding recess for receiving at least a portion of the protruding member when the plunger assembly is transitioned to the second position. The protruding member may be moved into a locked position within the recess by rotating the plunger rod relative to the stopper during transition of the plunger assembly from the first position to the second position. In a further configuration, the housing and the plunger rod each extend about the exterior surface of the syringe barrel to form a protective cover. In a further configuration, a medication or drug is disposed within the chamber of the syringe barrel.

According to another embodiment of the present invention, a syringe assembly includes a syringe barrel having a first end, a second end, and a sidewall extending therebetween having an exterior surface and an interior surface defining a chamber therein. The syringe assembly also includes a stopper disposed within the chamber and a plunger assembly. The plunger assembly includes an elongated plunger rod, a housing, and a handle portion connecting the elongated plunger rod and the handle portion. The plunger assembly may be adapted to transition from a first position wherein the plunger rod and housing extend over the exterior surface of the syringe barrel to form a protective cover, to a second position wherein the plunger rod rotatably engages a plunger head to advance the stopper within the chamber.

In certain configurations, the elongated plunger rod, the housing, and the handle portion are a unitary assembly. The unitary assembly may be proximally advanced over the syringe barrel prior to the rotational engagement of the plunger rod and the stopper. The stopper may include a plunger adapter and the plunger rod may engage the plunger adapter in the second position.

In yet another configuration, the plunger rod is configured to advance the stopper from a first position to a second position within the barrel, wherein the first position is different from the second position. The plunger rod may extend substantially parallel with the exterior surface of the syringe barrel in the first position, and may extend substantially in line with a longitudinal axis of the syringe barrel in the second position. A luer connection may also be engaged with the first end of the syringe barrel, and a cap may be adapted to seal the first end of the syringe barrel.

An optional tamper evident band may also be disposed over a portion of the cap and the plunger assembly.

In another configuration, the plunger rod includes a protruding member adjacent a distal end, and the stopper includes a corresponding recess for receiving at least a portion of the protruding member when the plunger assembly is transitioned to the second position. The protruding member may be moved into a locked position within the recess by rotating the plunger rod relative to the stopper during transition of the plunger assembly from the first position to the second position.

According to another embodiment of the present invention, a syringe assembly includes a syringe barrel having a first end, a second end, and a sidewall extending therebetween having an exterior surface and an interior surface defining a chamber therein extending along a longitudinal axis of the syringe barrel. The syringe assembly also includes a stopper disposed within the chamber and an outwardly extending flange disposed about at least a portion of the exterior surface of the syringe barrel. The flange may extend radially outward therefrom in a direction substantially perpendicular to the longitudinal axis. The syringe assembly may also include a plunger rod having a distal end and a proximal end, with the plunger rod transitionable from a first position in which the distal end contacts the outwardly extending flange, to a second position in which the distal end engages a portion of the stopper.

The stopper may include a plunger adapter and the plunger rod may engage the plunger adapter in the second position. The plunger rod may also include a protruding member adjacent the distal end, and the stopper may include a corresponding recess for receiving at least a portion of the protruding member when the plunger assembly is transitioned to the second position.

Further details and advantages of the invention will become clear upon reading the following detailed description in conjunction with the accompanying drawing figures, wherein like parts are designated with like reference numerals throughout.

BRIEF DESCRIPTION OF THE DRAWINGS

FIG. 4 is a left side view of the syringe assembly of FIG. 1 in accordance with an embodiment of the present invention.

FIG. 5 is a top view of the syringe assembly of FIG. 1 in accordance with an embodiment of the present invention.

FIG. 6 is a bottom view of the syringe assembly of FIG. 1 in accordance with an embodiment of the present invention.

FIG. 7 is a cross-sectional view of the syringe assembly of FIG. 1 taken along line 7-7 of FIG. 6 in accordance with an embodiment of the present invention.

DESCRIPTION OF PREFERRED EMBODIMENTS

Figure 1:
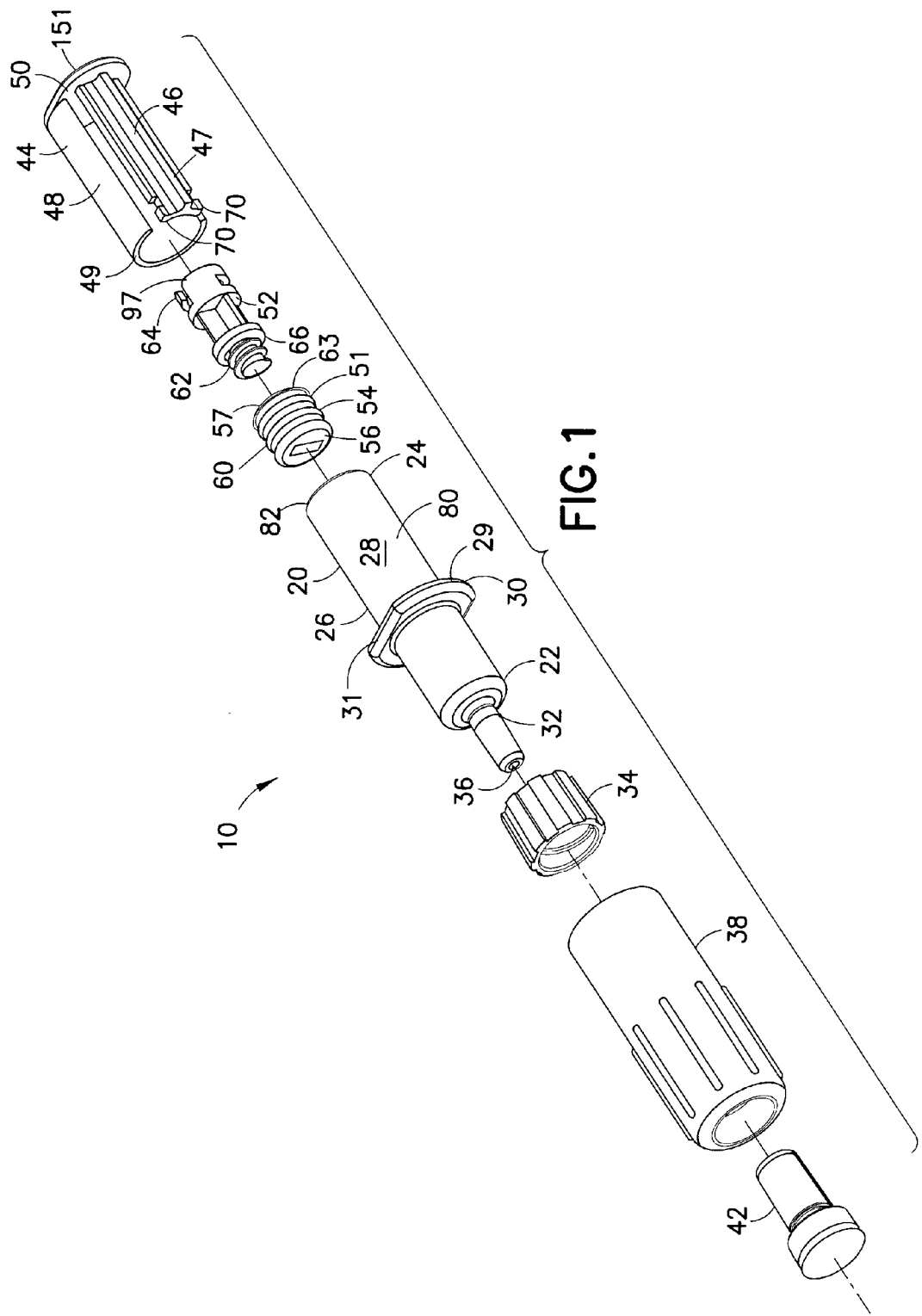
FIG. 1 is an exploded perspective view of a syringe assembly in accordance with an embodiment of the present invention.

For purposes of the description hereinafter, spatial orientation terms, if used, shall relate to the referenced embodiment as it is oriented in the accompanying drawing figures or otherwise described in the following detailed description. However, it is to be understood that the embodiments described hereinafter may assume many alternative variations and embodiments. It is also to be understood that the specific devices illustrated in the accompanying drawing figures and described herein are simply exemplary and should not be considered as limiting.

Referring to FIG. 1-15, a syringe assembly, generally indicated as 10, adapted for the dispensing and delivery of a fluid is shown. Syringe assembly 10 is intended for use for injection or infusion of fluid, such as a medication, directly into a patient, and is generally shown and described for purposes of the present description as a hypodermic syringe. Syringe assembly 10 is contemplated for use in connection with a needle such as by connecting syringe assembly 10 to a separate needle assembly (not shown), or alternatively for connection with a separate intravenous (IV) connection assembly (not shown).

The syringe assembly 10 includes a syringe barrel 20 having a first or distal end 22 and a second or proximal end 24, with a sidewall 26 extending therebetween and defining an interior chamber 28 of the syringe barrel 20. The syringe barrel 20 has an exterior surface 80 and an interior surface 82 as defined by sidewall 26. The sidewall 26 may be centered along the longitudinal axis of the syringe barrel 20. The syringe barrel 20 may be in the general fowl of an elongated cylindrical barrel, as is known in the art for the general shape of a hypodermic syringe, although other forms for containing a fluid for delivery are also contemplated by the present invention. The syringe barrel 20 may be formed of glass, or may be injection molded from thermoplastic material such as polypropylene and polyethylene according to techniques known to those of ordinary skill in the art, though it is to be appreciated that the syringe barrel 20 may be made from other suitable materials and according to other applicable techniques. In certain configurations, the syringe barrel 20 may include an outwardly extending flange 30 about at least a portion of the syringe barrel between the first end 22 and the second end 24 of the syringe barrel 20. In several embodiments, the flange 30 is substantially centered between the first end 22 and the second end 24 of the syringe barrel 20. The flange 30 may be configured for easy grasping by a medical practitioner, as will be discussed herein.

The syringe barrel 20 may include markings, such as graduations on the sidewall 26 thereof, for providing an indication as to the level or amount of fluid contained within the syringe barrel 20. Such markings may be provided on the external wall, the internal wall, or integrally formed or otherwise within the sidewall 26 of syringe barrel 20. Alternatively, or in addition thereto, the markings may provide a description of the contents of the syringe, or other identifying information, as may be known in the art.

The first or distal end 22 of syringe barrel 20 includes an outlet opening 36 which may have a profile adapted for engagement with a separate dispensing device, such as a needle assembly or IV connection assembly. In one embodiment, the first or distal end 22 may include a generally tapered luer connection 32, for engagement with an optional separate tapered luer structure (not shown), as is generally known. The outlet opening 36 of the syringe barrel 20 is provided in fluid communication with the chamber 28 and may be adapted to communicate with a needle cannula (not shown). A tip cap 34 including a plug 42 for sealing the outlet opening 36 may be provided over the outlet opening 36 in the initial pre-use position to maintain the sterility of the contents of the chamber 28. A secondary protective cover 38 may also be provided over the distal end 22 of the syringe barrel 20 providing a secondary cover for the outlet opening 36.

An outwardly extending flange 30 may also be provided about a portion of the sidewall 26 of the syringe barrel 20 to assist a medical practitioner in the handling of the syringe assembly 10. The outwardly extending flange 30 may extend radially outward from the exterior surface of the sidewall 26 of the syringe barrel 20. In certain configurations, the outwardly extending flange 30 may be discontinuous about a portion of the sidewall 26. In other configurations, the outwardly extending flange may have at least one flattened edge 31 to allow the syringe assembly 10 to be placed on a flat surface, such as a counter, without rolling Referring again to FIGS. 1-15, a stopper 54 is slideably disposed within the chamber 28 of the syringe barrel 20. In an initial pre-use position, as shown in FIGS. 2-9, the stopper 54 of the syringe assembly 10 is positioned within the interior chamber 28 of the syringe barrel 20 at a position adjacent to the second or proximal end 24 of the syringe barrel 20. A plunger adapter 52 may be secured to the stopper 54 via an engagement of a stopper engaging portion 62 and a corresponding adapter engaging portion 63, as shown in FIG. 1. In one embodiment, the plunger adapter 52 and the stopper 54 are co-formed such that the stopper 54 includes the plunger adapter 52.

In one embodiment, the stopper 54 has a first end 56 and a second end 57 and includes an elongate body 60 that is generally cylindrical. In one embodiment, the elongate body 60 of the stopper 54 may define the adapter engaging portion 63 configured to receive the stopper engaging portion 62 of the plunger adapter 52. The stopper 54 may include a threaded portion 66 positioned within the adapter engaging portion 63 that is configured to receive and engage a corresponding threaded portion of the stopper engaging portion 62 of the plunger adapter 52. The elongate body 60 of the stopper 54 also includes one or more annular ribs 51 extending about an exterior surface of the stopper 54 for providing sealing engagement with the interior surface of the sidewall 26 of the syringe barrel 20.

The syringe assembly 10 also includes a plunger assembly 44. The plunger assembly 44 includes an elongated plunger rod 46, a housing 48, and a handle portion 50 connecting the plunger rod 46 and the housing 48. In one configuration, the elongate plunger rod 46, the housing 48, and the handle portion 50 are a unitary assembly with the elongate plunger rod 46 and the handle portion 50 each extending from a first surface 151 of the handle portion 50.

Figure 2:
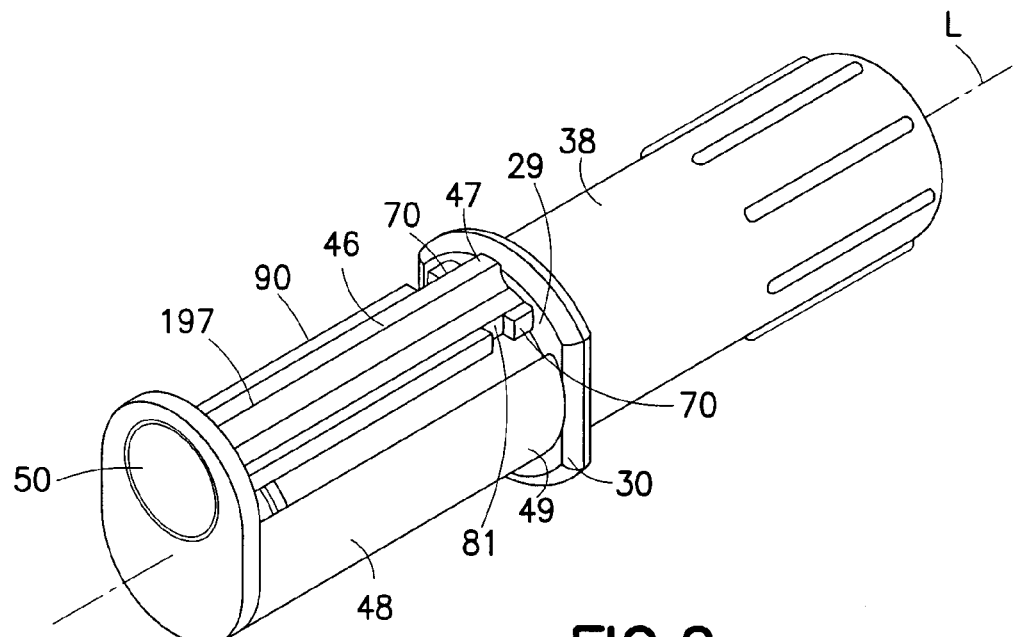
FIG. 2 is a perspective view of the syringe assembly of FIG. 1 in a first pre-use position in accordance with an embodiment of the present invention.
Figure 3:
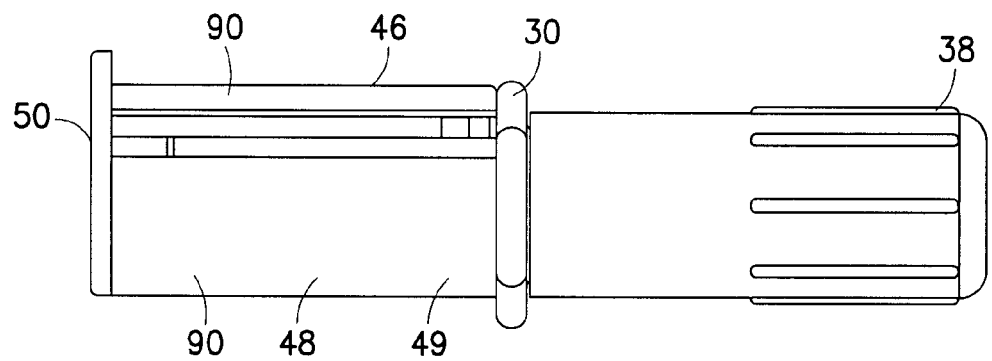
FIG. 3 is a right side view of the syringe assembly of FIG. 1 in accordance with an embodiment of the present invention.
Figure 8:
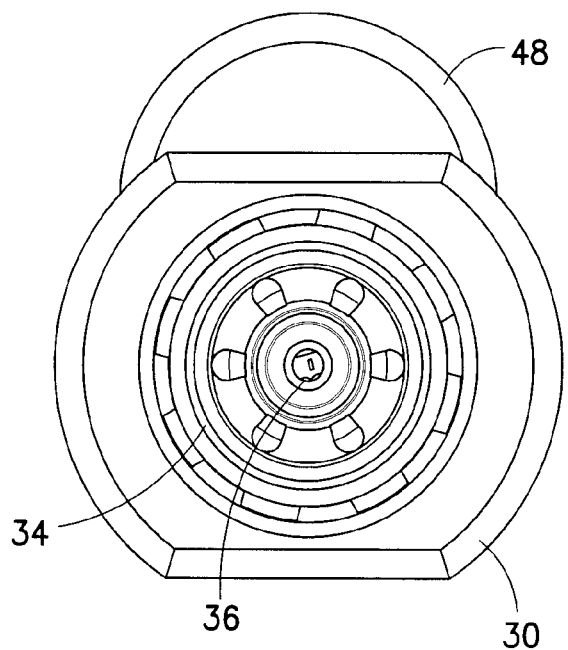
FIG. 8 is a front view of the syringe assembly of FIG. 1 in accordance with an embodiment of the present invention.
Figure 9:
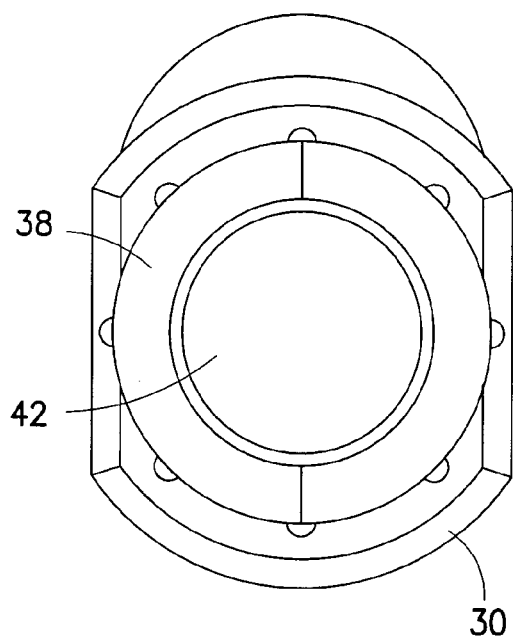
FIG. 9 is a rear view of the syringe assembly of FIG. 1 in accordance with an embodiment of the present invention.

The plunger assembly 44 is adapted to transition from a first initial position, as shown in FIGS. 2-9, to a second ready-to-use position, as shown in FIGS. 10-15. In the initial position, the plunger assembly 44 is disposed about the exterior surface of the syringe barrel 20. In one configuration, the elongate plunger rod 46 and the housing 48 are circumferentially disposed about the exterior surface of the syringe barrel 20. In another configuration, the housing 48 extends substantially about the exterior surface 80 of the syringe barrel 20 in a "c-shape". In still a further configuration, the housing 48 and the elongate plunger rod 46 extend along the exterior surface 80 of the syringe barrel 20 in a plane that is substantially parallel to a longitudinal axis L of the syringe barrel 20, as shown in FIG. 2. In still a further configuration, the housing 48 and the elongate plunger rod 46 form a protective cover 90 at least partially enclosing the first or distal end 22 of the syringe barrel 20. In another configuration, the housing 48 and the elongate plunger rod 46 form a protective cover 90 substantially enclosing the first or distal end 22 of the syringe barrel 20. In yet another configuration, a distal end 49 of the housing 48 and a distal end 47 of the elongate plunger rod 46 engage a proximal surface 29 of the outwardly extending flange 30 in the initial position, as shown in FIGS. 2-9.

In the second, ready-to-use position, as shown in FIGS. 10-15, the plunger assembly 44 is configured such that the elongate plunger rod 46 engages a portion of the stopper 54. In this position, the plunger assembly 44 is removed from the position shown in FIGS. 2-9 in which the plunger assembly 44 is disposed about an exterior surface of the syringe barrel 20 and is re-engaged with the syringe assembly 10 by engaging a portion of the elongate plunger rod 46 with a corresponding portion of the stopper 54 and/or adapter 52.

Figure 10:
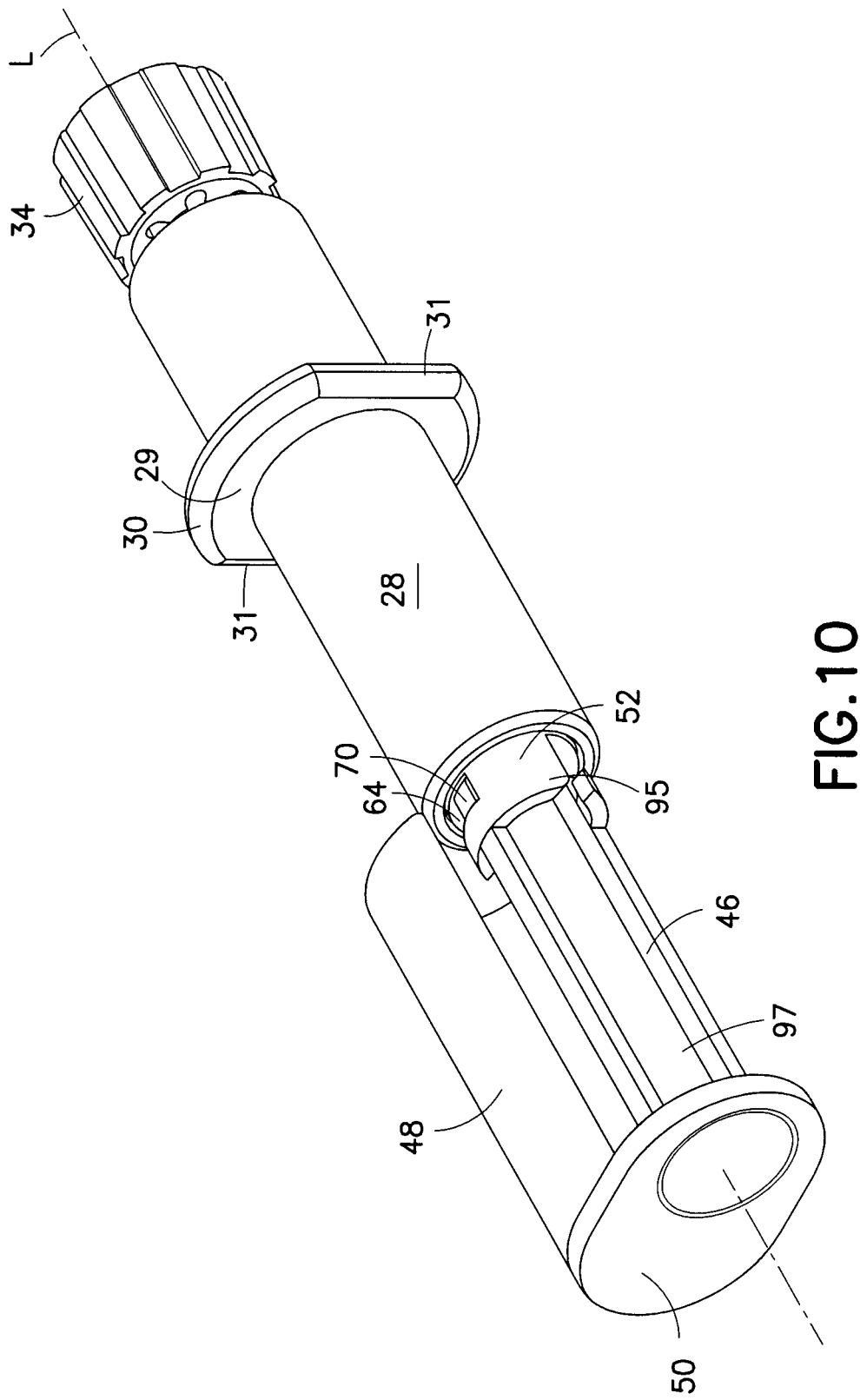
FIG. 10 is a perspective view of the syringe assembly of FIG. 1 in a second ready-to-use position in accordance with an embodiment of the present invention.
Figure 11:
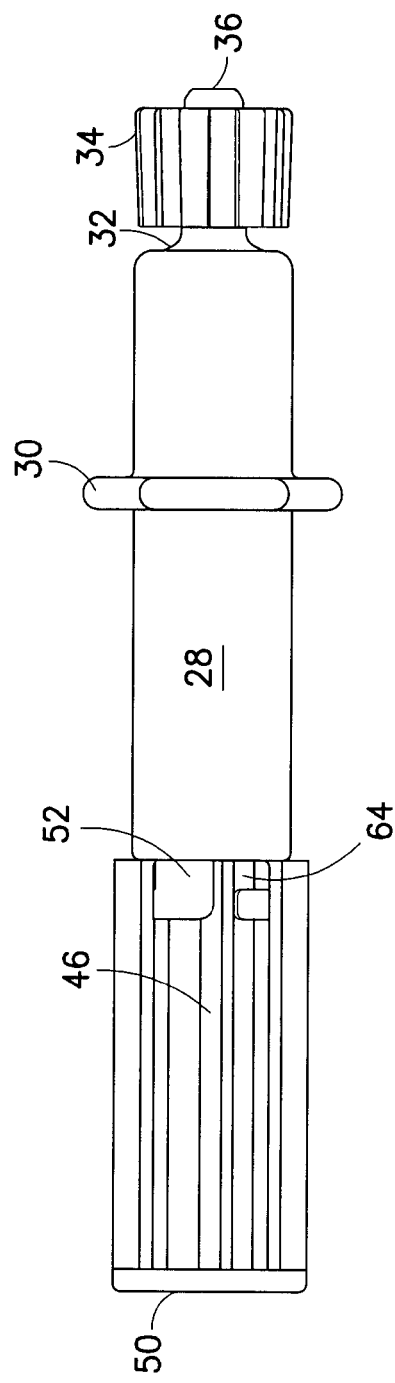
FIG. 11 is a right side view of the syringe assembly of FIG. 10 in accordance with an embodiment of the present invention.
Figure 12:
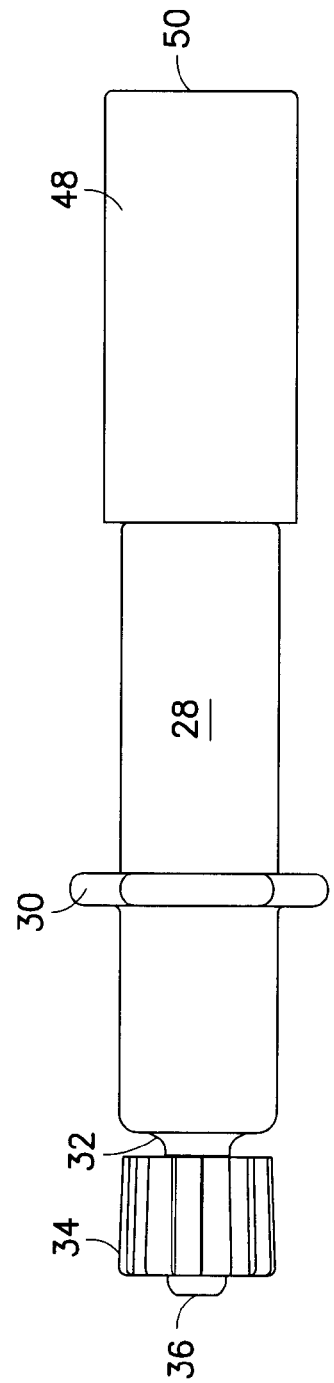
FIG. 12 is a left side view of the syringe assembly of FIG. 10 in accordance with an embodiment of the present invention.
Figure 13:
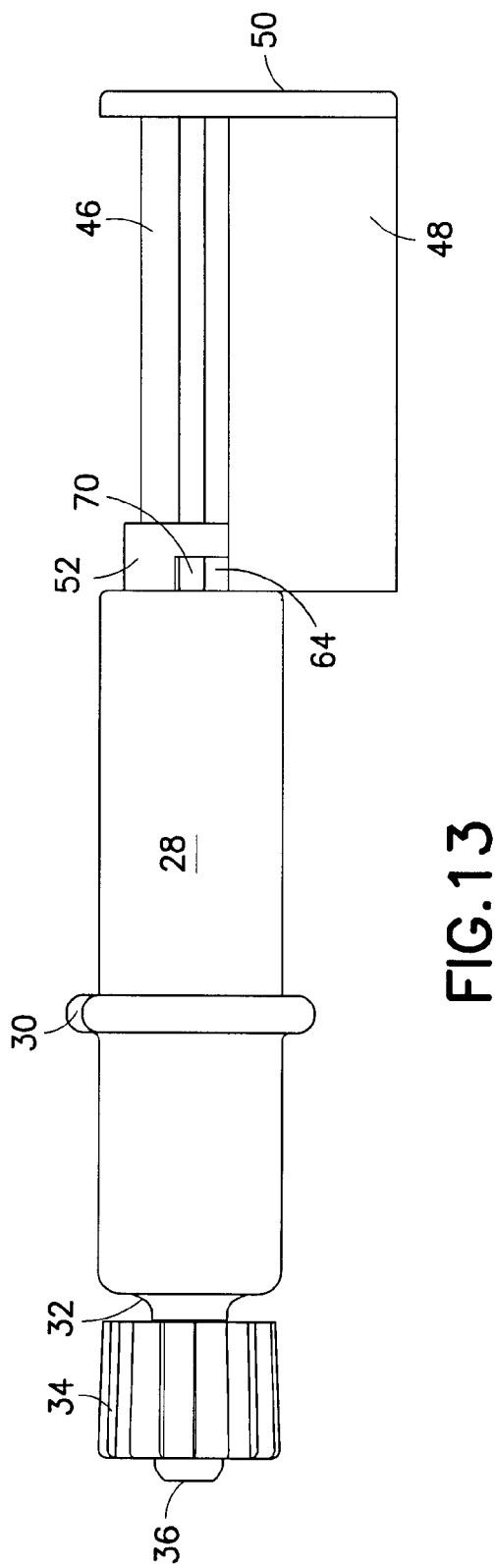
FIG. 13 is a top view of the syringe assembly of FIG. 10 in accordance with an embodiment of the present invention.
Figure 14:
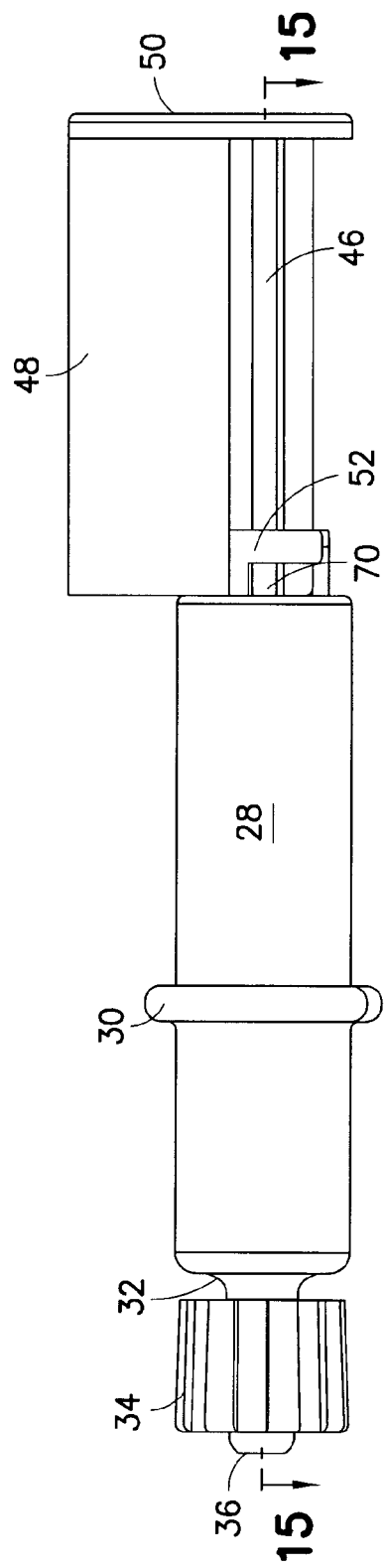
FIG. 14 is a bottom view of the syringe assembly of FIG. 10 in accordance with an embodiment of the present invention.
Figure 15:
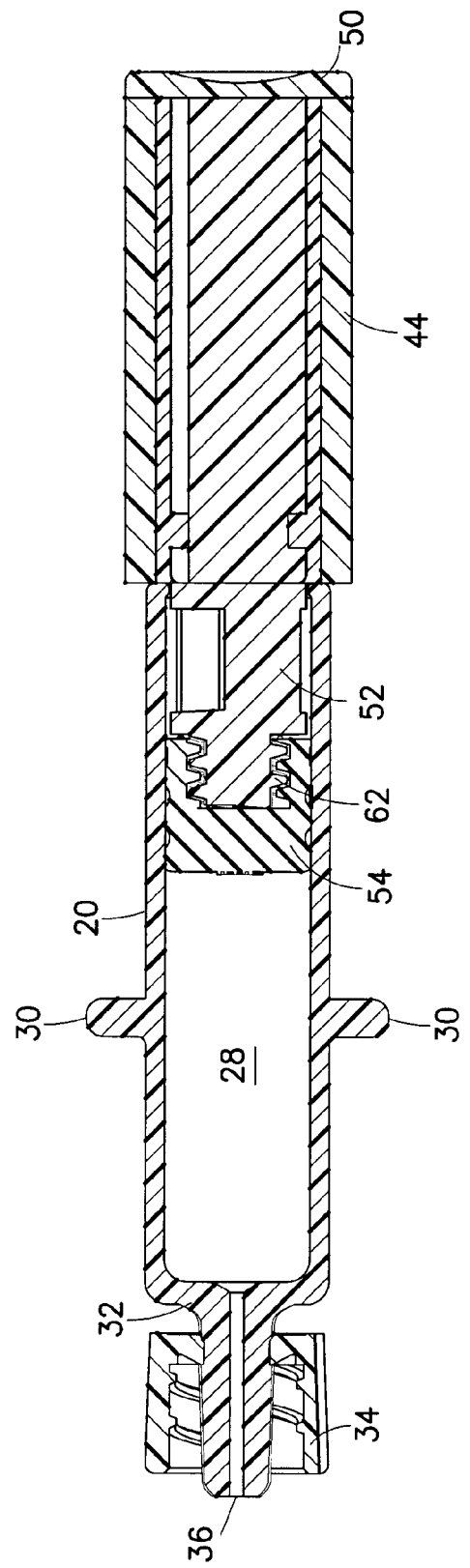
FIG. 15 is a cross-sectional view of the syringe assembly of FIG. 10 taken along line 15-15 of FIG. 14 in accordance with an embodiment of the present invention.

As shown specifically in the initial position in FIG. 2, the distal end 47 of the elongate plunger rod 46 may include at least one protruding member 70 extending therefrom for engaging a corresponding recess 64, as shown in FIG. 10, defined within the stopper 54 and/or adapter 52. In one configuration, the protruding member 70 may be formed adjacent a receiving notch 81, such that receiving notch 81 is defined within the distal end 47 of the elongate plunger rod 46 and is disposed between a body 197 of the plunger rod 46 and the protruding member 70. The protruding member 70 may be formed substantially in-line with the plunger rod 46 and may include an interior surface substantially corresponding to an interior surface of the housing 48 so as to form a substantially continuous surface about the exterior surface 80 of the syringe barrel 20. Similarly, it is noted that the distal end of the elongate plunger rod 46 may include a recess and the stopper 54 and/or adapter 52 may include a corresponding protrusion for engaging the recess.

In one configuration, the plunger rod 46 is substantially aligned along the longitudinal axis L, as shown in FIG. 10, and engaged with the stopper 54 in the ready-to-use position. In certain configurations in which the stopper 54 includes a stopper adapter 52 engaged therewith, the elongate plunger rod 46 may engage the stopper adapter 52.

Figure 16:
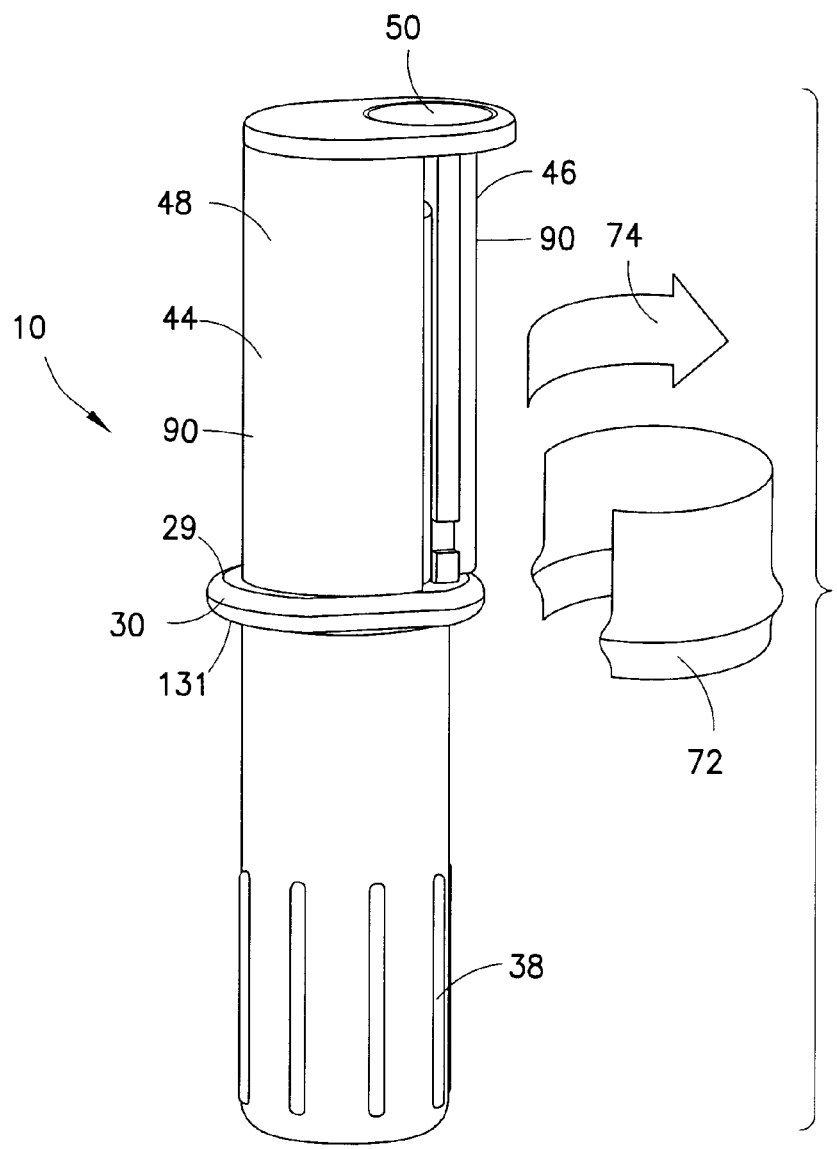
FIG. 16 is a perspective view of the syringe assembly of FIG. 1 in a pre-use position having a tamper evident band associated therewith in accordance with an embodiment of the present invention.
Figure 17:
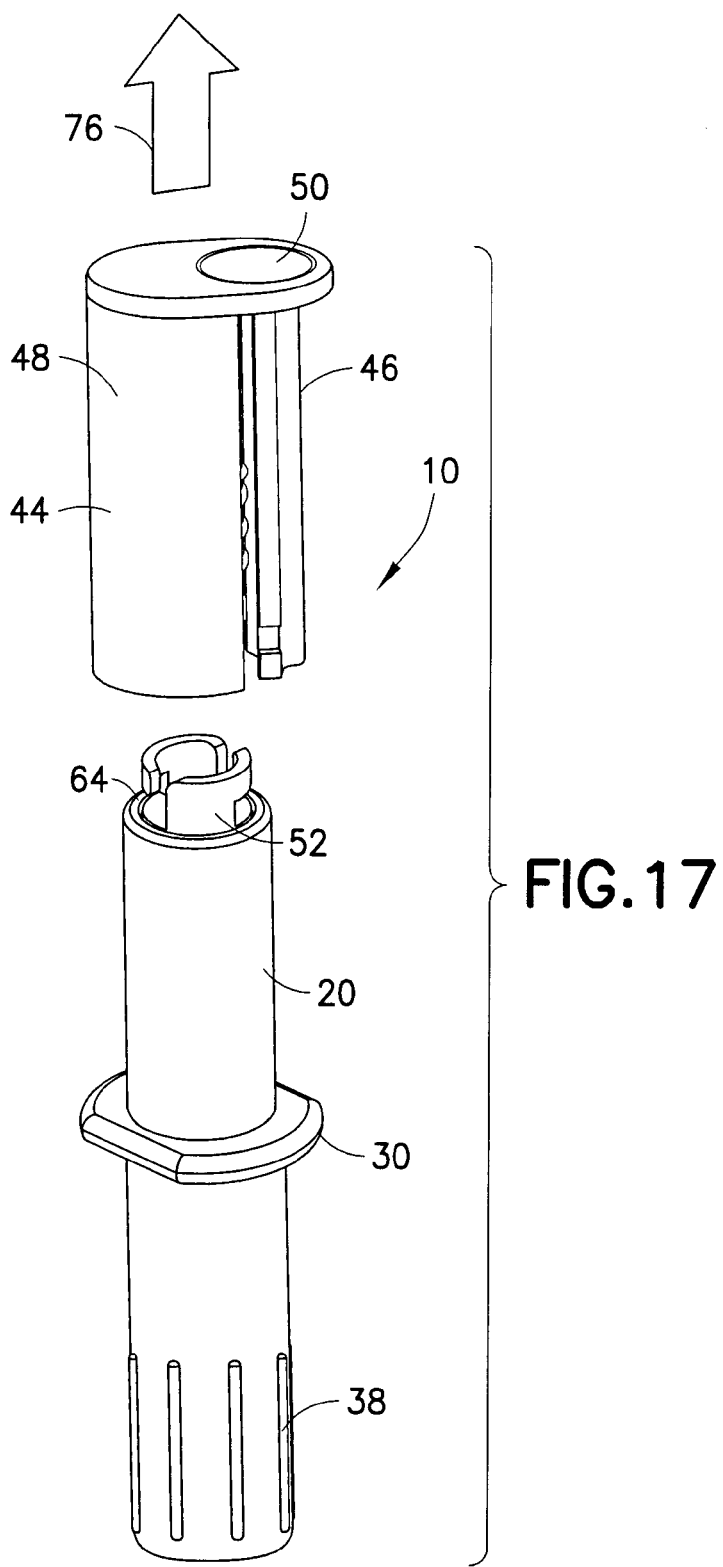
FIG. 17 is a perspective view of the syringe assembly of FIG. 16 having the plunger assembly removed therefrom in accordance with an embodiment of the present invention.

In use, a medical practitioner will transition the syringe assembly 10 from an initial pre-use position, as shown in FIG. 16, to an intermediate position in which the plunger assembly 44 is removed from engagement with the remainder of the syringe assembly 10, as shown in FIG. 17. In the initial position, as shown in FIG. 16, the syringe assembly 10 may include a tamper evident band 72 disposed over a portion of the secondary protective cover 38 and the plunger assembly 44. The tamper evident band 72 may provide a further sealing mechanism to maintain the sterility of the interior of the syringe assembly 10, such as to maintain the sterility of the chamber 28 of the syringe barrel 20 prior to use. The tamper evident band 72 may be formed of any material suitable to provide a sufficient seal over a portion of the protective cover 38 and a portion of the plunger assembly 44. The tamper evident band 72 is formed of a breakable material that may not be reattached over the syringe assembly 10 once access to the interior of the syringe assembly 10 has been initiated. A medical practitioner may remove the tamper evident band 72 by applying a tearing force to the tamper evident band 72 in the direction of arrow 74, as shown in FIG. 16.

Once the tamper evident band 72 has been removed from the syringe assembly 10, the interface between the protective cover 90 and the proximal surface 29 of the outwardly extending flange 30 is shown. In certain configurations, the interface between the secondary protective cover 38 and a distal surface 131 of the outwardly extending flange 30 may also be shown. A medical practitioner may then proximally advance the plunger assembly 44 over the syringe barrel 20 in the direction of arrow 76, as shown in FIG. 17, to separate the plunger assembly 44 from the syringe barrel 20. In one embodiment, a portion of the plunger assembly 44 and/or the outwardly extending flange 30 and/or the syringe barrel 20 may include a conventional detent arrangement to prevent inadvertent disengagement between the syringe barrel 20 and the plunger assembly 44 prior to the intentional advancement of the plunger assembly 44 over the syringe barrel 20 by a medical practitioner.

Figure 18:
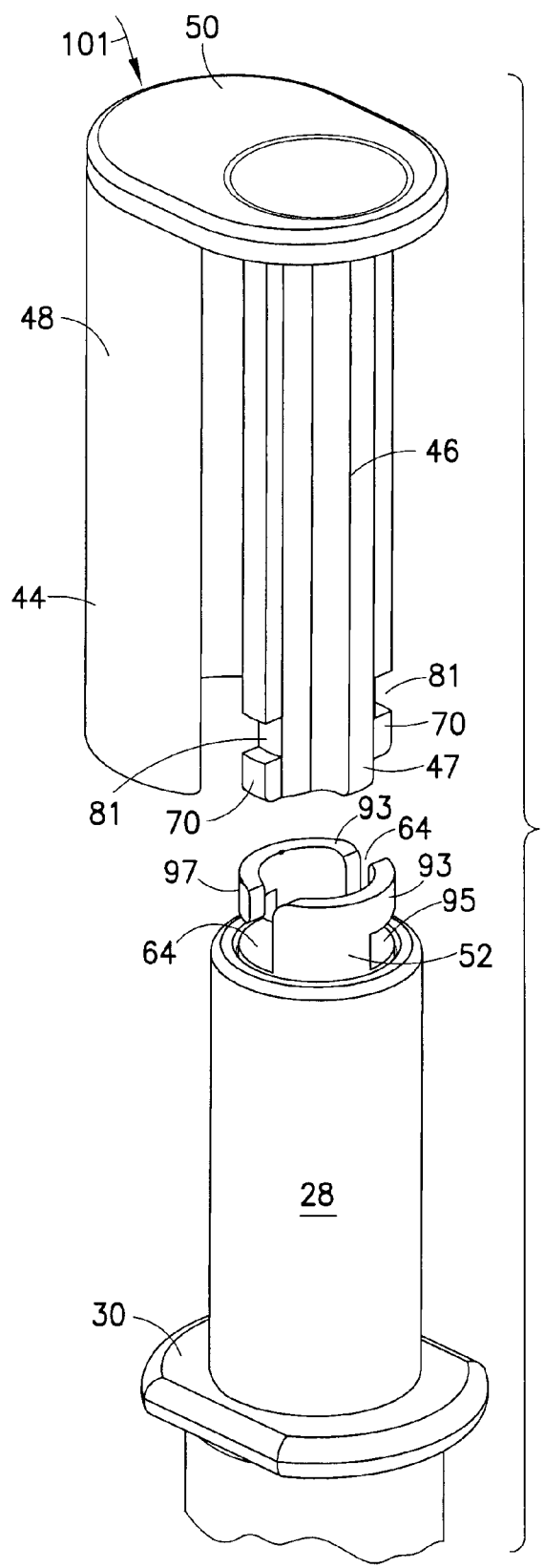
FIG. 18 is a partial perspective view of the plunger assembly and a plunger adapter of the syringe assembly of FIG. 16 in accordance with an embodiment of the present invention.
Figure 19:
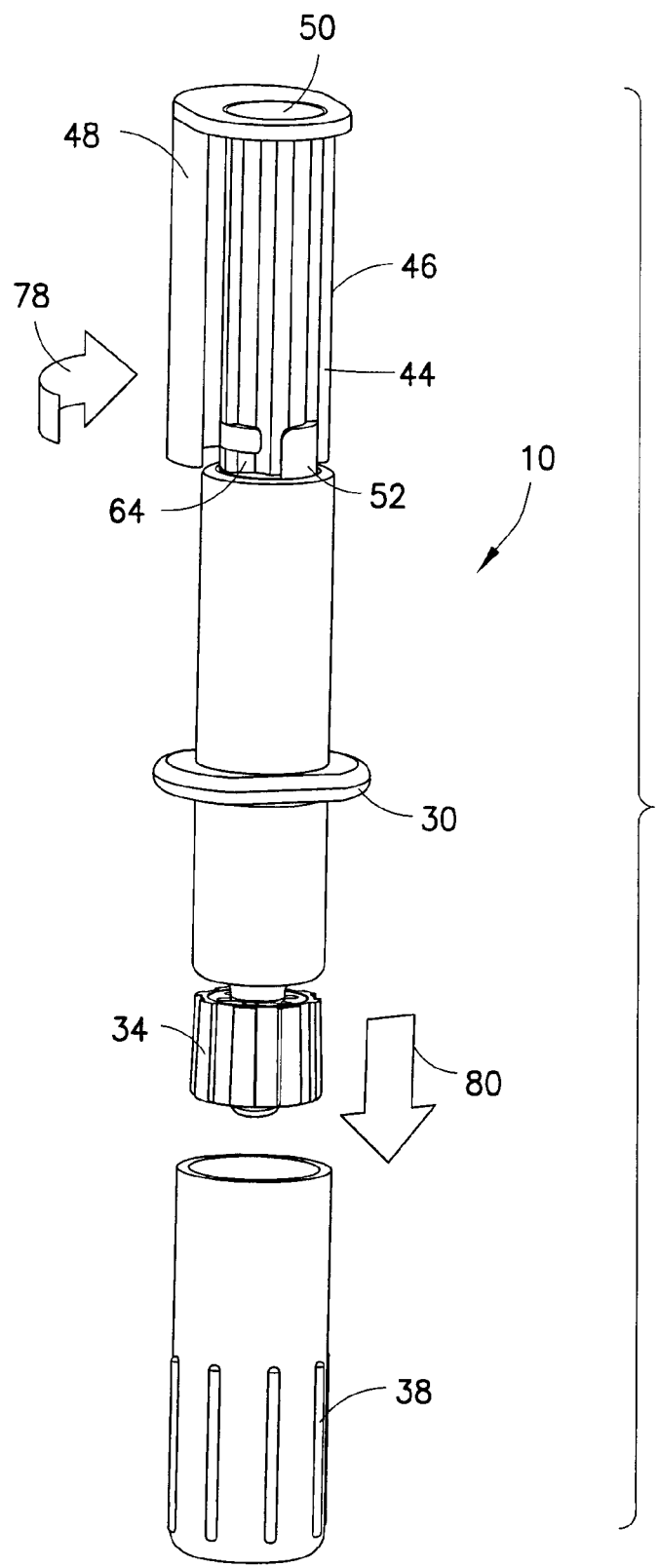
FIG. 19 is a perspective view of the syringe assembly of FIG. 16 having the plunger assembly engaged with a portion of the stopper in the ready-to-use position in accordance with an embodiment of the present invention.

Referring to FIGS. 18-19, once the plunger assembly 44 is removed from the syringe barrel 20, the medical practitioner may align the plunger rod 46 of the plunger assembly 44 with the plunger adapter 52. As discussed above, the protruding member 70 of the distal end 47 of the plunger rod 46 may be aligned with the corresponding recess 64 disposed within the plunger adapter 52. The plunger adapter 52 may include a restraining tab 93 configured to define a slot 95 within a proximal end 97 of the plunger adapter 52 and communicate with the recess 64. When a downward force is applied to the plunger assembly 44 aligned with the plunger adapter 52 in the direction of arrow 101, as shown in FIG. 18, the protruding member 70 of the plunger rod 46 is received within the recess 64 of the adapter 52. A user may then apply a rotational force in the direction of arrow 78, as shown in FIG. 19, to the plunger assembly 44 to rotate the plunger rod 46 with respect to the adapter 52, thereby causing the protruding member 70 to be received within and advanced along slot 95. Restraining tab 93 may be received within receiving notch 81 of the plunger rod 46 such that the plunger rod 46 and the adapter 52 are coupled together in a locked position.

In one embodiment, the plunger rod 46 includes two protruding members 70 disposed on substantially opposing sides of the distal end 47 of the plunger rod 46 and oriented in substantially the same plane, as shown in FIG. 18. A receiving notch 81 may be disposed adjacent each of the protruding members, as discussed above. The adapter 52 may also include two corresponding restraining tabs 93 and slots 95 adapted to each receive a protruding member 70 therein. In one embodiment, each of the restraining tabs 93 may be oriented to extend about the proximal end 97 of the adapter 52, such as in a direction extending substantially about the perimeter of the proximal end 97. It is further contemplated herein that a plurality of protruding members 70 and corresponding recesses 64 may be provided within the plunger rod 46 and the adapter 52 to secure the plunger assembly 44 with the adapter 52.

Figure 20:
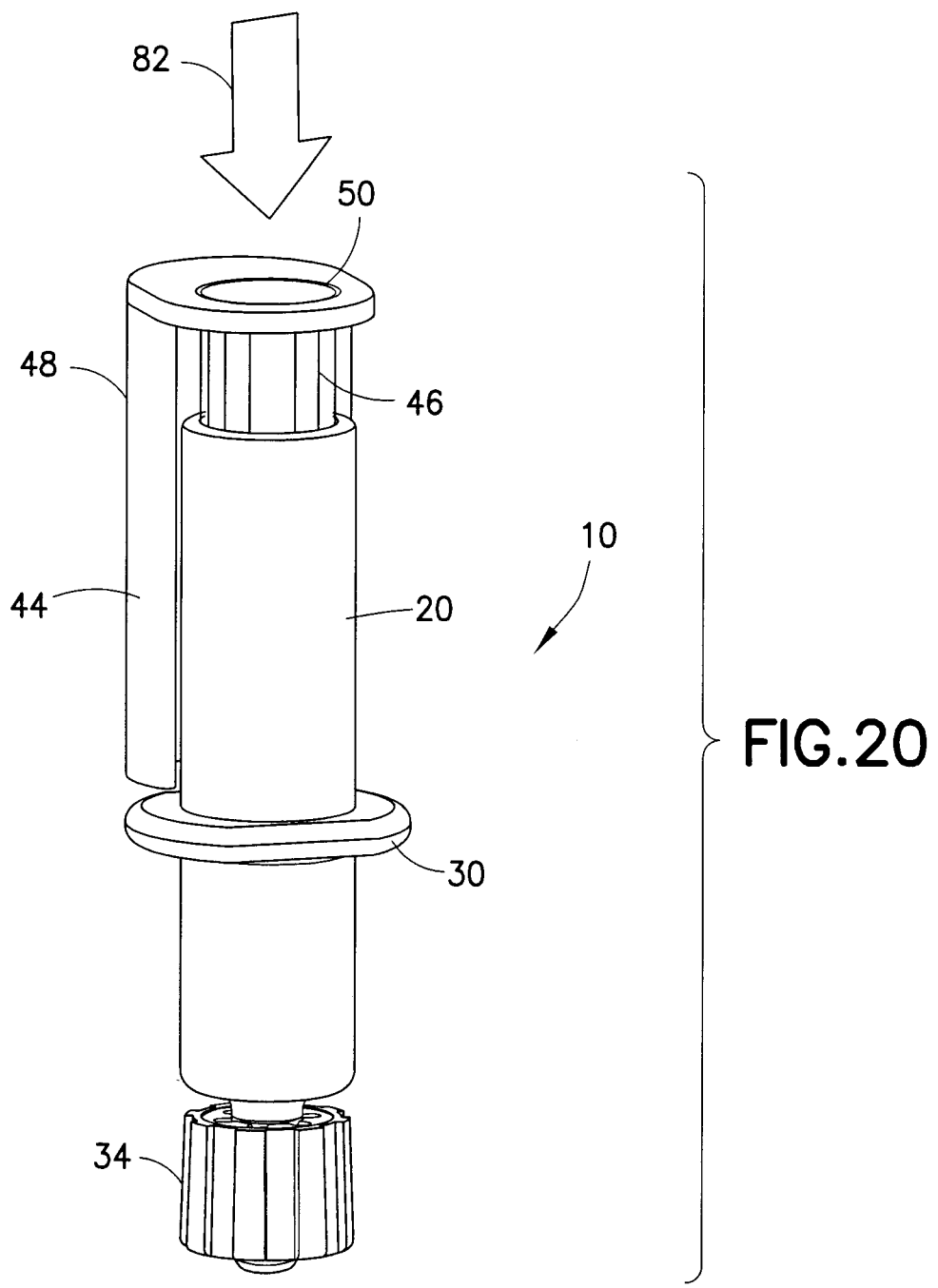
FIG. 20 is a perspective view of the syringe assembly of FIG. 16 in the used position in accordance with an embodiment of the present invention.

Referring again to FIG. 19, once the plunger rod 46 has been rotationally engaged with the adapter 52, the medical practitioner may remove the protective cover 38 from the distal end of the syringe assembly 10 by applying a downward force in the direction of arrow 180, as shown in FIG. 19, to the protective cover 38. The medical practitioner may then expel the contents of the chamber 28 of the syringe barrel 20 by applying a downward force in the direction of arrow 182, as shown in FIG. 20, to the handle portion 50 of the plunger assembly 44 to advance the plunger rod 46 coupled to the adapter 52 to advance the stopper 54, as shown in FIG. 1, within the chamber 28 from a first position to a second position. In one embodiment, the chamber 28 may include a medication or drug disposed therein and the advancement of the plunger rod 46 in the direction of arrow 182 advances the stopper 54 within the chamber 28 to expel the medication or drug therefrom.

It is to be appreciated that the syringe assembly 10 according to the present embodiment is particularly suitable for use as a pre-filled syringe with the stopper 54 initially provided at the second or proximal end 24 of the syringe barrel 20. Alternatively, the plunger rod 46 could be used to pull a stopper 54 positioned adjacent the first or distal end 22 of the syringe barrel 20 so as to aspirate an empty syringe barrel 20. Syringe assembly 10 may be further provided with a mechanism so as to prevent re-use of the device. For example, the engagement between plunger rod 46 and stopper 54 as provided through protruding members 70 of plunger rod 46 and plunger adapter 52 may be a one-way engagement, intended to prevent re-use. It is also to be appreciated that the syringe assembly 10 according to the present embodiment allows for the overall length of a pre-filled syringe to be minimized for packaging and storage savings and to reduce storage space in secure medication containment drawers.

While embodiments of a syringe assembly having a removable cover for use as a plunger rod have been described in the foregoing detailed description, those skilled in the art may make modifications and alterations to these embodiments without departing from the scope and spirit of the invention. Accordingly, the foregoing description is intended to be illustrative rather than restrictive. The invention described hereinabove is defined by the appended claims and all changes to the invention that fall within the meaning and the range of equivalency of the claims are embraced within their scope.

The invention claimed is:

1. A syringe assembly, comprising:
   a syringe barrel having a first end, a second end, and a sidewall extending therebetween having an exterior surface and an interior surface defining a chamber therein;
   a stopper disposed within the chamber; and
   a plunger assembly comprising an elongated plunger rod, a housing, and a handle portion connecting the elongated plunger rod and the housing,
   wherein the plunger assembly is adapted to transition from a first position in which the plunger assembly is disposed about the exterior surface of the syringe barrel, to a second position in which the plunger rod is engaged with the stopper, wherein transition of the plunger assembly from the first position to the second position comprises rotational engagement of the plunger rod with a portion of the stopper, and
   wherein the plunger assembly is proximally advanced over the syringe barrel prior to the rotational engagement of the plunger rod and the stopper.

2. The syringe assembly of claim 1, wherein the elongated plunger rod, the housing, and the handle portion are a unitary assembly.

3. The syringe assembly of claim 1, wherein the stopper comprises a plunger adapter and the plunger rod engages the plunger adapter in the second position.

4. The syringe assembly of claim 1, wherein the plunger rod is configured to advance the stopper from the first position to the second position within the syringe barrel, wherein the first position is different from the second position.

5. The syringe assembly of claim 1, wherein the plunger rod extends substantially parallel with the exterior surface of the syringe barrel in the first position and extends substantially in line with a longitudinal axis of the syringe barrel in the second position.

6. The syringe assembly of claim 1, further comprising a luer connection engaged with the first end of the syringe barrel, and a cap adapted to seal the first end of the syringe barrel.

7. The syringe assembly of claim 6, further comprising a tamper evident band disposed over a portion of the cap and the plunger assembly.

8. The syringe assembly of claim 1, wherein the plunger rod comprises a protruding member adjacent a distal end, and the stopper comprises a corresponding recess for receiving at least a portion of the protruding member when the plunger assembly is transitioned to the second position.

9. The syringe assembly of claim 8, wherein the protruding member is moved into a locked position within the recess by rotating the plunger rod relative to the stopper during transition of the plunger assembly from the first position to the second position.

10. The syringe assembly of claim 1, wherein the housing and the plunger rod each extend about the exterior surface of the syringe barrel to form a protective cover.

11. The syringe assembly of claim 1, further comprising a medication or drug within the chamber.

12. A syringe assembly, comprising:
    a syringe barrel having a first end, a second end, and a sidewall extending therebetween having an exterior surface and an interior surface defining a chamber therein;
    a stopper disposed within the chamber; and
    a plunger assembly comprising an elongated plunger rod, a housing, and a handle portion connecting the elongated plunger rod and the housing,
    wherein the plunger assembly is adapted to transition from a first position, wherein the plunger rod and housing extend over the exterior surface of the syringe barrel to form a protective cover, to a second position, wherein the plunger rod rotatably engages a plunger head to advance the stopper within the chamber, and
    wherein the plunger assembly is proximally advanced over the syringe barrel prior to the rotational engagement of the plunger rod and the stopper.

13. The syringe assembly of claim 12, wherein the elongated plunger rod, the housing, and the handle portion are a unitary assembly.

14. The syringe assembly of claim 12, wherein the stopper comprises a plunger adapter and the plunger rod engages the plunger adapter in the second position.

15. The syringe assembly of claim 12, wherein the plunger rod is configured to advance the stopper from the first position to the second position within the syringe barrel, wherein the first position is different from the second position.

16. The syringe assembly of claim 12, wherein the plunger rod extends substantially parallel with the exterior surface of the syringe barrel in the first position and extends substantially in line with a longitudinal axis of the syringe barrel in the second position.

17. The syringe assembly of claim 12, further comprising a luer connection engaged with the first end of the syringe barrel, and a cap adapted to seal the first end of the syringe barrel.

18. The syringe assembly of claim 17, further comprising a tamper evident band disposed over a portion of the cap and the plunger assembly.

19. The syringe assembly of claim 12, wherein the plunger rod comprises a protruding member adjacent a distal end, and the stopper comprises a corresponding recess for receiving at least a portion of the protruding member when the plunger assembly is transitioned to the second position.

20. The syringe assembly of claim 19, wherein the protruding member is moved into a locked position within the recess by rotating the plunger rod relative to the stopper during transition of the plunger assembly from the first position to the second position.

21. A syringe assembly comprising:
- a syringe barrel having a first end, a second end, and a sidewall extending therebetween having an exterior surface and an interior surface defining a chamber therein extending along a longitudinal axis of the syringe barrel;
- a stopper disposed within the chamber;
- an outwardly extending flange disposed about at least a portion of the exterior surface of the syringe barrel and extending radially outward therefrom in a direction substantially perpendicular to the longitudinal axis; and
- a plunger rod having a distal end and a proximal end, the plunger rod transitionable from a first position in which the distal end contacts the outwardly extending flange, to a second position in which the distal end engages a portion of the stopper.

22. The syringe assembly of claim 21, wherein the stopper comprises a plunger adapter and the plunger rod engages the plunger adapter in the second position.

23. The syringe assembly of claim 21, wherein the plunger rod comprises a protruding member adjacent the distal end, and the stopper comprises a corresponding recess for receiving at least a portion of the protruding member when the plunger rod is transitioned to the second position.

* * * * *